(12) United States Patent
Buchanan et al.

(10) Patent No.: US 12,296,313 B2
(45) Date of Patent: *May 13, 2025

(54) SYSTEM AND METHOD FOR FORMULATING MEDICAL TREATMENT EFFLUENTS

(71) Applicant: MILTON ROY, LLC, Warminster, PA (US)

(72) Inventors: Walter Riley Buchanan, Lenexa, KS (US); Grant William Forsee, Kansas City, MO (US)

(73) Assignee: MILTON ROY, LLC, Davidson, NC (US)

( * ) Notice: Subject to any disclaimer, the term of this patent is extended or adjusted under 35 U.S.C. 154(b) by 1111 days.

This patent is subject to a terminal disclaimer.

(21) Appl. No.: 17/181,766

(22) Filed: Feb. 22, 2021

(65) Prior Publication Data

US 2021/0178355 A1  Jun. 17, 2021

Related U.S. Application Data

(63) Continuation-in-part of application No. 16/205,844, filed on Nov. 30, 2018, now Pat. No. 11,452,982.
(Continued)

(51) Int. Cl.
*B01J 19/08* (2006.01)
*A61L 2/14* (2006.01)
(Continued)

(52) U.S. Cl.
CPC .............. *B01J 19/088* (2013.01); *A61L 2/14* (2013.01); *A61L 2/18* (2013.01); *C02F 1/46109* (2013.01);
(Continued)

(58) Field of Classification Search
CPC .............. B01J 19/088; B01J 2219/0809; B01J 2219/0884; B01J 2219/0894;
(Continued)

(56) References Cited

U.S. PATENT DOCUMENTS 4,283,291 A   8/1981  Lowther
4,399,016 A   8/1983  Tsukada
(Continued)

OTHER PUBLICATIONS

"International Search Report and Written Opinion", International Application No. PCT/US2016/053919, Dec. 23, 2016.
(Continued)

*Primary Examiner* — Xiuyu Tai
(74) *Attorney, Agent, or Firm* — Edell, Shapiro & Finnan, LLC

(57) ABSTRACT

A system and method for formulating a medical treatment effluent by performing plasma reactions creating a plasma area in a gas adjacent to a liquid. An embodiment of the plasma reactor includes a housing with an internal reaction chamber, first and second inlet paths to the reaction chamber, and electrodes for producing an electric field. The system may optionally further include a pre-ionization electrode and pre-ionization electric field for pre-ionizing a feed gas prior to entry into a reaction chamber. The reactor uses plasma to ionize gas adjacent with the liquid. The ionized gas reacts with the liquid to form an effluent. Exemplary medical treatments include: immunization (immuno) therapy; wound treatment; cancer treatment; and disinfectant applications.

8 Claims, 13 Drawing Sheets

Related U.S. Application Data which is a continuation-in-part of application No. 16/027,005, filed on Jul. 3, 2018, now Pat. No. 10,882,021, which is a continuation-in-part of application No. 15/277,093, filed on Sep. 27, 2016, now Pat. No. 10,010,854.

(60) Provisional application No. 62/235,750, filed on Oct. 1, 2015.

(51) Int. Cl.
*A61L 2/18* (2006.01)
*C02F 1/461* (2023.01)

(52) U.S. Cl.
CPC .............. *B01J 2219/0809* (2013.01); *B01J 2219/0884* (2013.01); *B01J 2219/0894* (2013.01); *C02F 2303/04* (2013.01)

(58) Field of Classification Search
CPC ......... B01J 19/1887; B01J 19/22; A61L 2/14; A61L 2/18; C02F 1/46109; C02F 2303/04; C02F 1/4608; C02F 1/04; C02F 1/30; C02F 2103/10; H01J 37/32761; H01J 37/32348; H01J 37/32568; H01J 37/32596; H01J 37/32541; H01J 37/324; H01J 37/32; H05H 1/48; H05H 1/3468
See application file for complete search history.

(56) References Cited

U.S. PATENT DOCUMENTS

| | | | |
|---|---|---|---|
| 5,311,419 A | 5/1994 | Shires | |
| 5,387,842 A | 2/1995 | Roth et al. | |
| 5,399,832 A | 3/1995 | Tanisaki et al. | |
| 5,414,324 A | 5/1995 | Roth | |
| 5,872,426 A | 2/1999 | Kunhardt et al. | |
| 5,900,103 A | 5/1999 | Tomoyasu et al. | |
| 5,959,412 A | 9/1999 | Ushijima | |
| 6,005,349 A | 12/1999 | Khnhardt et al. | |
| 6,069,539 A | 5/2000 | Sanders et al. | |
| 6,105,518 A | 8/2000 | Robson et al. | |
| 6,118,218 A | 9/2000 | Yializis et al. | |
| 6,147,452 A | 11/2000 | Kunhardt et al. | |
| 6,167,239 A | 12/2000 | Wright et al. | |
| 6,170,668 B1 | 1/2001 | Babko-Malyi | |
| 6,208,529 B1 | 3/2001 | Davidson | |
| 6,353,846 B1 | 3/2002 | Fleeson | |
| 6,429,400 B1 | 8/2002 | Sawada | |
| 6,433,480 B1 | 8/2002 | Stark et al. | |
| 6,441,553 B1 | 8/2002 | Yializis | |
| 6,489,585 B1 | 12/2002 | Nakamura et al. | |
| 6,633,109 B2 | 10/2003 | Falkenstein | |
| 6,664,737 B1 | 12/2003 | Berry et al. | |
| 6,700,787 B1 | 3/2004 | Beseth et al. | |
| 6,773,335 B2 | 8/2004 | Yanobe et al. | |
| 6,818,193 B2 | 11/2004 | Christodoulatos et al. | |
| 6,826,222 B2 | 11/2004 | Hill | |
| 6,842,122 B1 | 1/2005 | Langner et al. | |
| 6,853,138 B1 | 2/2005 | Park et al. | |
| 6,946,793 B1 | 9/2005 | Nelson | |
| 6,999,022 B1 | 2/2006 | Vesel et al. | |
| 7,098,420 B2 | 8/2006 | Crow et al. | |
| 7,215,697 B2 | 5/2007 | Hill | |
| 7,221,102 B2 | 5/2007 | Kotani et al. | |
| 7,273,995 B1 | 9/2007 | Manz et al. | |
| 7,399,944 B2 | 7/2008 | Devries et al. | |
| 7,507,934 B2 | 3/2009 | Kondou et al. | |
| 7,737,867 B2 | 6/2010 | Arthur et al. | |
| 7,764,140 B2 | 7/2010 | Nagarkatti et al. | |
| 7,796,954 B2 | 9/2010 | Whitaker Filho | |
| 8,081,933 B2 | 12/2011 | Malaga et al. | |
| 8,089,026 B2 | 1/2012 | Sellers | |
| 8,093,758 B2 | 1/2012 | Hussman | |
| 8,254,869 B2 | 8/2012 | Hyde et al. | |
| 8,542,076 B2 | 9/2013 | Maier | |
| 8,633,782 B2 | 1/2014 | Nagarkatti et al. | |
| 8,710,926 B2 | 4/2014 | Nagarkatti et al. | |
| 9,106,313 B2 | 8/2015 | Ueki | |
| 9,287,800 B2 | 3/2016 | Hruska et al. | |
| 9,394,189 B2 | 7/2016 | Hruska et al. | |
| 9,419,581 B2 | 8/2016 | Mckinzie | |
| 9,420,679 B2 | 8/2016 | Cheung et al. | |
| 9,573,698 B1 | 2/2017 | He | |
| 9,665,645 B2 | 5/2017 | Hawley | |
| 9,692,392 B2 | 7/2017 | Cabanillas et al. | |
| 9,698,748 B2 | 7/2017 | Manssen et al. | |
| 9,704,405 B2 | 7/2017 | Kashi et al. | |
| 9,736,920 B2 | 8/2017 | Smith et al. | |
| 9,819,410 B1 | 11/2017 | Azevedo et al. | |
| 2002/0000019 A1 | 1/2002 | Park et al. | |
| 2003/0039297 A1 | 2/2003 | Wittle et al. | |
| 2003/0049183 A1 | 3/2003 | Sharma et al. | |
| 2003/0067273 A1 | 4/2003 | Benjamin et al. | |
| 2004/0084382 A1 | 5/2004 | Ryazanova | |
| 2004/0094401 A1 | 5/2004 | Carlow | |
| 2004/0183461 A1 | 9/2004 | Kane et al. | |
| 2004/0245087 A1 | 12/2004 | Lee | |
| 2005/0260354 A1 | 11/2005 | Singh et al. | |
| 2006/0097811 A1 | 5/2006 | Nakamura et al. | |
| 2006/0150911 A1 | 7/2006 | Miyairi et al. | |
| 2006/0208650 A1 | 9/2006 | Kondou | |
| 2008/0060579 A1 | 3/2008 | Hsieh | |
| 2008/0159925 A1 | 7/2008 | Shimizu et al. | |
| 2008/0292497 A1 | 11/2008 | Vangeneugden et al. | |
| 2009/0153279 A1 | 6/2009 | Chen | |
| 2010/0123502 A1 | 5/2010 | Bhutta et al. | |
| 2010/0171428 A1 | 7/2010 | Kirchmeier et al. | |
| 2010/0219757 A1 | 9/2010 | Benzerrouk et al. | |
| 2010/0310434 A1 | 12/2010 | Buchanan et al. | |
| 2011/0241798 A1 | 10/2011 | Hong et al. | |
| 2011/0284437 A1 | 11/2011 | Johnson et al. | |
| 2012/0020844 A1 | 1/2012 | Foret et al. | |
| 2012/0250370 A1 | 10/2012 | Taniguchi et al. | |
| 2012/0262064 A1 | 10/2012 | Nagarkatti et al. | |
| 2013/0194224 A1 | 8/2013 | Lai | |
| 2014/0178604 A1 | 6/2014 | Selwyn | |
| 2014/0246364 A1 | 9/2014 | Hruska | |
| 2014/0246381 A1 | 9/2014 | Buchanan et al. | |
| 2015/0022795 A1 | 1/2015 | Coenen et al. | |
| 2015/0251933 A1* | 9/2015 | Nakamura ............ C02F 1/4608 210/192 |
| 2016/0028311 A1 | 1/2016 | Murakami | |
| 2016/0030910 A1 | 2/2016 | Biberger et al. | |
| 2016/0194224 A1 | 7/2016 | Buchanan et al. | |
| 2016/0197564 A1 | 7/2016 | Buchanan et al. | |
| 2017/0095788 A1 | 4/2017 | Buchanan | |
| 2017/0312362 A1 | 11/2017 | Hybertson et al. | |
| 2018/0050800 A1 | 2/2018 | Boykin et al. | |
| 2018/0053501 A1 | 2/2018 | Hilal et al. | |
| 2018/0302807 A1 | 10/2018 | Chen et al. | |
| 2018/0311639 A1 | 11/2018 | Buchanan et al. | |
| 2020/0027457 A1 | 1/2020 | Gelinske et al. | |
| 2020/0082645 A1 | 3/2020 | Shaw et al. | |

OTHER PUBLICATIONS

"International Search Report and Written Opinion; PCT/US2019/0450473".

"International Search Report and Writter Opinion", PCT/US2014/016730, Jul. 4, 2015, pp. 1-18.

Schulz, et al., "Concentration fields near air-water interfaces during interfacial mass transport: oxygen transport and random square wave analysis", Braz. J. Chem. Eng. vol. 26 No. 3 Sao Paulo Jul./Sep. 2009, Jul.-Sep. 2009, 527-536.

Extended European Search Report for European Patent Application No. 22205904.0 dated Aug. 4, 2023, 6 pages.

Communication Pursuant to Article 94(3) for European Application No. 19830254.9 dated Oct. 17, 2023, 6 pages.

(56) References Cited

OTHER PUBLICATIONS

Communication Pursuant to Article 94(3) for European Application No. 19830254.9 dated Jul. 4, 2024, 5 pages.

* cited by examiner

Production Rate of Hydrogen Peroxide and Hydrogen

| Feed Gas | Grams/kWh $H_2O_2$ | Grams/kWh $H_2$ |
|---|---|---|
| Argon | 1.70 | 0.10 |
| Argon/Hydrogen | 4.26 | 0.25 |

SYSTEM AND METHOD FOR FORMULATING MEDICAL TREATMENT EFFLUENTS

CROSS-REFERENCE TO RELATED APPLICATIONS

This application is a continuation-in-part of and claims priority in U.S. patent application Ser. No. 16/205,844, filed Nov. 30, 2018, which is a continuation-in-part of U.S. patent application Ser. No. 16/027,005, filed Jul. 3, 2018, which is a continuation-in-part of U.S. patent application Ser. No. 15/277,093, filed Sep. 27, 2016, now U.S. Pat. No. 10,010,854, which claims priority in U.S. Provisional Patent Application Ser. No. 62/235,750, filed Oct. 1, 2015. The contents of the aforementioned applications are incorporated by reference herein in their entireties.

BACKGROUND OF THE INVENTION

1. Field of the Invention

Embodiments of the current invention relate to plasma reactors and methods and systems that utilize plasma reactors for formulating effluents for medical treatment applications.

2. Description of the Related Art

Plasma reactors may include at least two electrodes which are spaced apart. Typically, a voltage difference is applied to the electrodes and an electric field is established between them. A stream of gas may be introduced to the space between the electrodes such that it passes through the electric field. Exposure to the electric field generally ionizes the gas and creates a plasma. If a stream of liquid is also introduced to the space between the electrodes, the gas and liquid may form two layers flowing in parallel and a plasma may form in the gas and at the surface of the liquid and further, the ions resulting from the plasma may be injected into, or may otherwise enter into the liquid as it passes through the electric field. Plasma injection into liquid may be utilized for applications such as: in-line liquid hydrocarbon fuel reforming for hydrogen enrichment to improve the fuel economy of internal combustion engines; nitrogen fixing by direct nitrogen ion injection into water; destruction of high molecular weight hydrocarbons (proteins and pharmaceuticals) in drinking water; ammonia/nitrate sequestering for treatment of high nitrate content water; demineralization (water softening) for consumer and industrial markets; nitrification of water for agricultural use; pH modification of liquid streams; disinfection, oxygen and ozone injection; and other similar applications.

In previous reactors that utilize gas and liquid, an eductor design was described (e.g., U.S. Pat. Nos. 9,287,800 and 9,394,189, Buchanan et al.), which utilized a low pressure zone created by an eductor to enhance the introduction of gas into the reactor and enhance the creation of the plasma all around the area between the first electrode and the liquid. This new and novel laminar flow reactor allows for an increased area of plasma generation with the elimination of the need to adhere to the physical characteristics of an eductor. This new and novel design forces gas into the reactor creating a relatively high pressure zone of gas above the liquid, the area of plasma generation can be greatly extended and the effectiveness of the system enhanced. In addition, previous eductor based reactors required the second electrode be in close proximity and directly in contact with the liquid. In this reactor, the second electrode may contact the liquid but also may be placed in close proximity or further away from the first electrode. In systems where the liquid needs to be electrically isolated from the electrode, the second electrode may be dielectrically isolated from the liquid by a non-conductive layer.

The ionization energy of a gas, or the minimum energy required to produce a plasma of the gas, is the minimum amount of energy required to remove the most loosely bound electron, also known as the valence electron, of an isolated neutral atom, molecule, or ion of the gas. The ionization energy varies from gas-to-gas and with the form of the gas. These values are well-known to those skilled in the art. For example, the molar ionization energy of atomic nitrogen is approximately 1402.3 kJ mol−1, atomic oxygen is approximately 1313.9 kJ mol−1, and atomic argon is approximately 1520.6 kJ mol−1. However, in practice, producing ionized gases or plasmas generally requires dissociating molecules of the gas, stripping shared electrons so atoms dissociate, and holding the atoms in an ionized form.

In addition to injection of ionic constituents into a liquid, diffusion or infusion of non-ionic gas constituents into a liquid can be an important component in various industries, including, but not limited to, many agricultural systems and nitrogen mitigation or removal systems. Many of these applications require increased oxygen or other gas constituents in water. Present methods for oxygen diffusion into water consist of diffusion via a bubbler or other type of aeration system. This type of diffusion can be enhanced but requires using higher pressure or alternative expensive methods to increase the amount of oxygen in the water. Further methods consist of forcing small oxygen bubbles through a membrane into water. However, each of these oxygen diffusion methods suffer from loss of significant amounts of oxygen, poor diffusion, and/or substantial monetary costs. Similarly, other systems that attempt to diffuse gas into liquids suffer from low diffusion rates, and saturation using traditional means is limited.

Studies using direct current (DC) electric fields and low frequency electric pulses in water have shown a positive effect on oxygen diffusion. For example, one such study is described in *Concentration fields near air-water interfaces during interfacial mass transport: oxygen transport and random square wave analysis*, by H. E. Schulz and J. G. Janzen, published in the Braz. J. Chem. Eng. Vol. 26 No. 3, São Paulo July/September 2009.

Non-thermal plasmas, which can be produced using a gas adjacent to a liquid in reactors such as those described in U.S. Pat. Nos. 9,287,800, 10,010,854, and 10,046,300, Buchanan et al., the contents of which are incorporated by reference herein, are formed infusing gases as ions into liquids. In these systems, such ions can be charged molecules or charged monatomic particles injected into a liquid stream. However, some applications benefit from the infusion of gas into liquid without major amounts of dissociation into monatomic ions. Thus, these systems benefit from molecular infusion or accelerated diffusion of a gas into a liquid.

For instance, in hydroponics, which is a method of growing plants without soil by using mineral nutrient solutions in a water solvent, oxygen levels of approximately 12 to 14 parts-per-million (PPM) are typically desirable. In some applications, levels as high as 50 PPM are desired. In Aquaponics, which combines conventional aquaculture, raising aquatic organisms in tanks, with hydroponics, maintaining high oxygen levels is often required for growth and good health of the species being raised.

In further applications, high levels of molecular gas infusion plus monatomic ionic injection is desired. For example, in hydroponic water treatment applications, a relatively low level of Oxidation Reduction Potential (ORP) may be desirable, such as approximately 350 to 500 mV. At the same time, high levels of dissolved oxygen in water is desirable for optimum plant health and growth.

What is needed is a simple, efficient, adjustable, low cost system and method for injecting or infusing a high level of a target gas into a liquid, whether flowing or stationary. Heretofore, there has not been a system and method for injecting particles from a gas into a liquid with the advantages of the present invention.

SUMMARY OF THE INVENTION

A first embodiment of the current invention provides a plasma laminar flow reactor comprising a housing, an electric field generator, an upper flow spreader, and a lower flow spreader. The housing may include an internal reactor chamber, a gas inlet port, and liquid inlet and liquid outlet ports. The electric field generator may include a first electrode, an optional pre-ionization electrode and a spaced apart second electrode and may generate an electric field or electric fields therebetween. The first electrode and optional pre-ionization electrode may be composed of one or more concentric shapes. A second electrode may have a shape similar to the first electrode or another shape depending on the application and the electrical nature of the liquid passing through the reactor. The second electrode may be spaced close to or spaced farther from the first electrode. In cases where the second electrode is not in close proximity to the first electrode, the second electrode may have any shape convenient to the design. Together, the first and second electrodes may produce a cylindrical electrical field close to the first electrode. The optional pre-ionization electrode may produce an electric field in close proximity to the field produced by the first electrode and second electrode. The plasma laminar flow reactor may also include a dielectric element positioned between the first electrode, the optional pre-ionization electrode, and the second electrode adjacent to the first electrode and optional pre-ionization electrode. The upper flow spreader may supply a stream of gas and liquid to the reactor chamber and may be positioned within the reactor chamber concentrically with the first electrode and the optional pre-ionization electrode. The lower flow spreader may supply a base for the stream of liquid as it flows to the reactor chamber and may be positioned within the reactor chamber concentrically with the first electrode and the upper flow spreader. The gas may create a gas zone inside the reactor chamber. The stream of liquid and the stream of gas may flow adjacent one another radially outward from the center of the reactor chamber and pass through the electric field. This may allow the gas and liquid to create and maintain two layers (gas over liquid) as the gas and liquid pass through the electric field. The gas may be injected from a relatively higher pressure gas source than the liquid through a flow limiting valve, small pump either as a steady flow or pulsed on and off, or other means well known to those familiar with gas control systems, such that the gas zone above the liquid is maintained.

A second embodiment of the current invention provides for an alteration of the second electrode by adding a dielectric isolation between the second electrode and the liquid. This may enable complete electrical isolation of the drive electronics and the liquid and gases to be used in the reactor. In addition, this may allow for plasma reactors without any conductive elements contacting the liquid.

A third embodiment of the current invention provides an alteration to the first electrode, the pre-ionization electrode, and/or the second electrode that can be used to modify the electrical characteristics of the reactor. This may enable larger reactors and more flexibility in design. In this embodiment the electrode is broken into several smaller electrodes. This may allow the plasma area to be larger without a proportional increase in the capacitance of the first electrode. This may be desirable for the voltage generator. The number of first or second electrodes may depend on the needs of the reactor and the reaction desired.

The present invention includes plasma reactor systems having a housing with an internal reaction chamber; at least one electric field generator configured for generating one or more electric fields between electrodes, with at least a portion of an electric field within the reaction chamber; a dielectric element; a gas source; a liquid source; a gas inlet path to the reaction chamber; and a liquid inlet path to the reaction chamber, where the stream of gas and stream of liquid within the reaction chamber are configured to flow adjacent one another and to pass through the electric field to produce an effluent.

Creating a plasma zone using a gas adjacent to a liquid accommodates many novel uses. These uses may include, but are not limited to, ionizing a gas and injecting the ionized particles into a liquid to create a new liquid; ionizing a gas and injecting ionized particles into a liquid to disinfect, oxidize, or otherwise modify the liquid in a desirable manner; ionizing a gas in order to dissociate molecules into their constituent atoms or different molecules in the gas to allow for undesirable atoms and/or molecules to enter a liquid and be removed from the gas stream; and ionizing a gas which modifies the molecules of the liquid in a desirable manner.

In another aspect of the present invention, a reactor system and method is configured for injecting or infusing ionized molecular particles, ionized monatomic particles, and/or non-ionized particles of a gas into a flowing or non-flowing liquid. The reactor includes a reaction chamber configured for holding a liquid and a gas adjacent to the liquid. A high intensity alternating current (AC) electric field is connected and applied to the reaction chamber, configured for making contact with the gas and/or the liquid. The voltage power level of the AC electric field is configured for adjustment as desired for optimizing desired gas particle injection, infusion, or diffusion into liquid. By varying the electrical field strength of these systems, the ratio of molecular infusion and ionic injection can be controlled. In embodiments of the present invention, the AC electric field may or may not ionize molecules in a gas or liquid and may terminate in a liquid. Moreover, the electric field may pass through a gas to be infused into a liquid while the gas is adjacent to the liquid and/or pass through the liquid. The present invention is configured for adjustment of the electric field to enhance the infusion of gas particles into liquid.

The system and method of the present invention can be utilized for producing medical treatment effluents. Exemplary medical treatments within the scope of the present invention include: immunization (immuno) therapy; wound treatment; cancer treatment; and disinfectant applications.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current invention will be apparent from the following detailed description of the embodiments and the accompanying drawing figures.

BRIEF DESCRIPTION OF THE DRAWINGS

Embodiments of the current invention are described in detail below with reference to the attached drawing figures, wherein.

Figure 1:
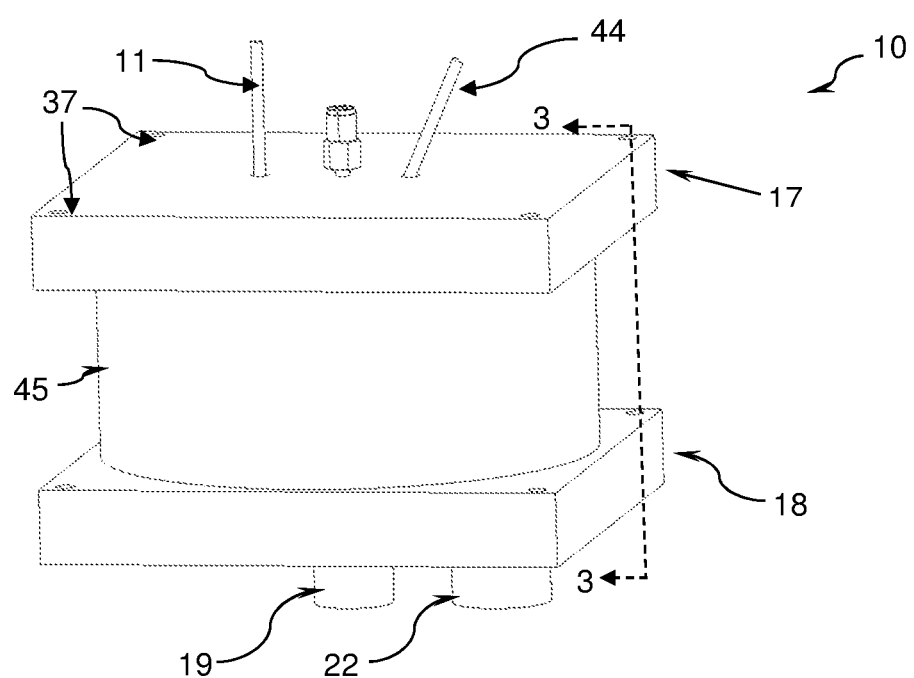
FIG. 1 is an isometric view of a plasma reactor constructed in accordance with various embodiments of the current invention.
Figure 2:
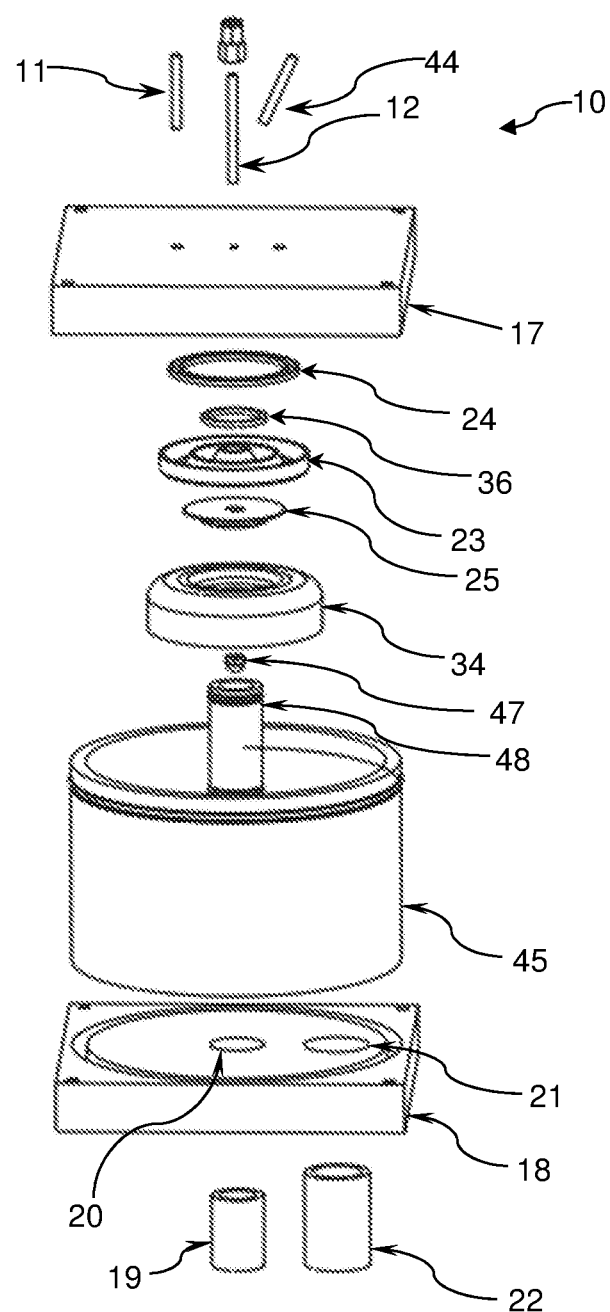
FIG. 2 is an exploded view of the plasma reactor of FIG. 1.
Figure 3:
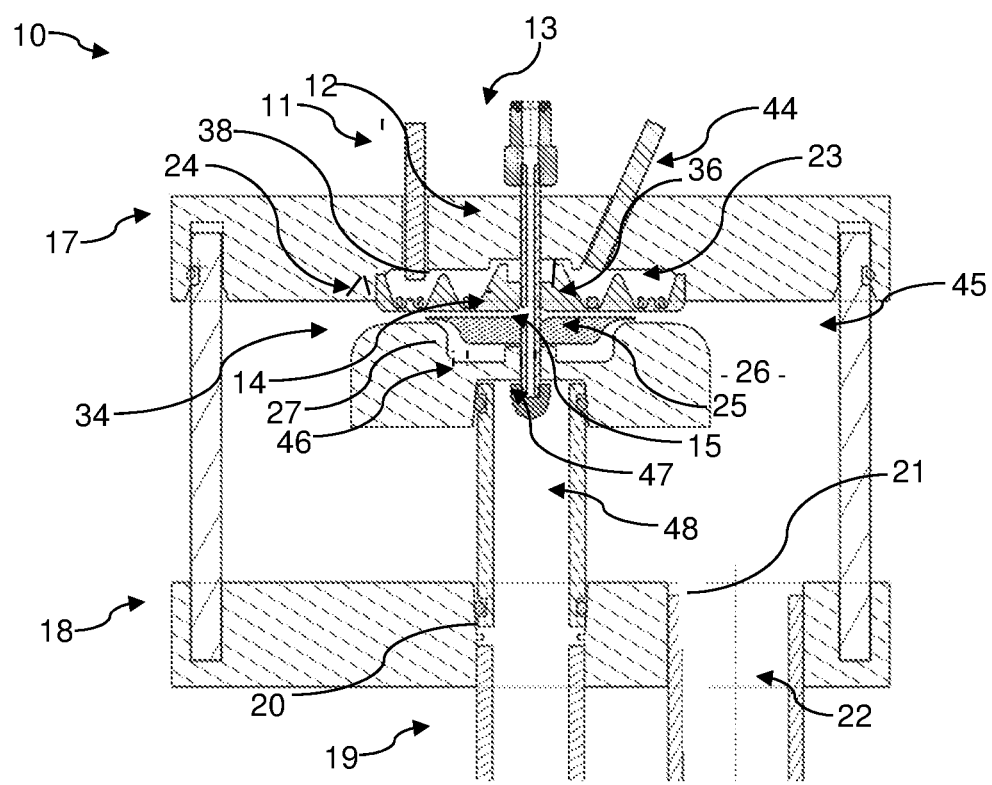
FIG. 3 is a cross sectional view of the plasma reactor of FIG. 1 cut along the line 3-3 of FIG. 1.
Figure 4:
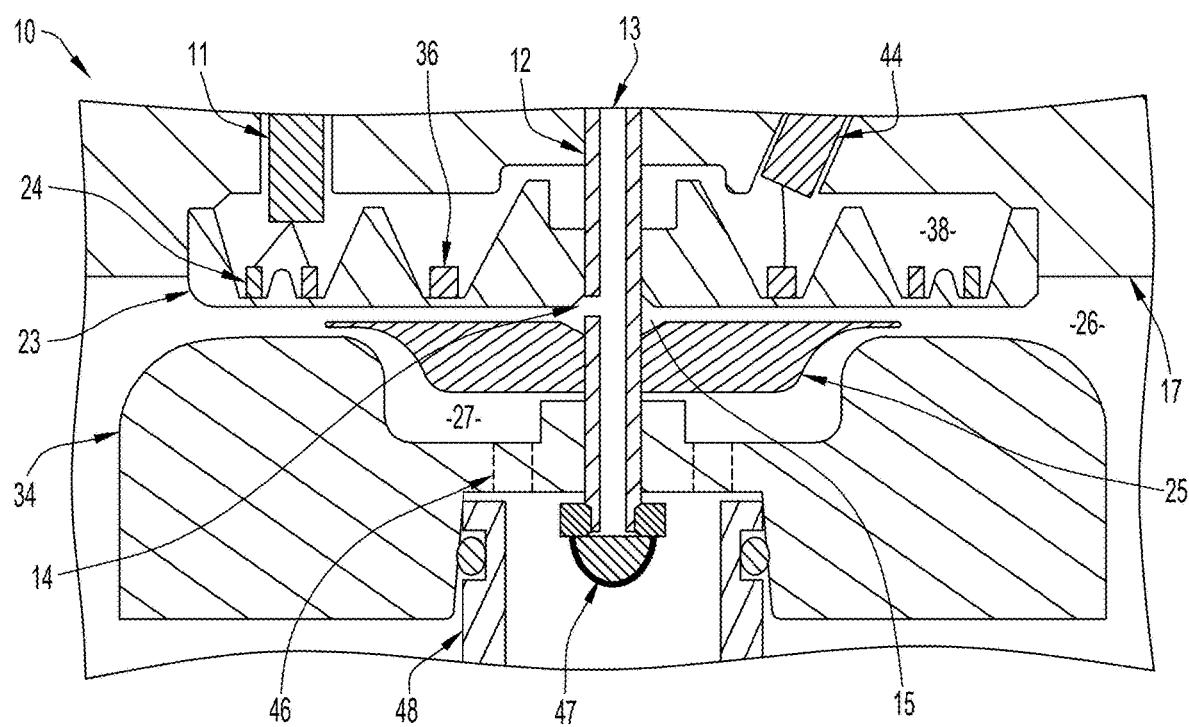
FIG. 4 is an enlarged cross sectional view of a plasma reactor from FIG. 3 highlighting the upper portion of a reactor chamber.
Figure 5:
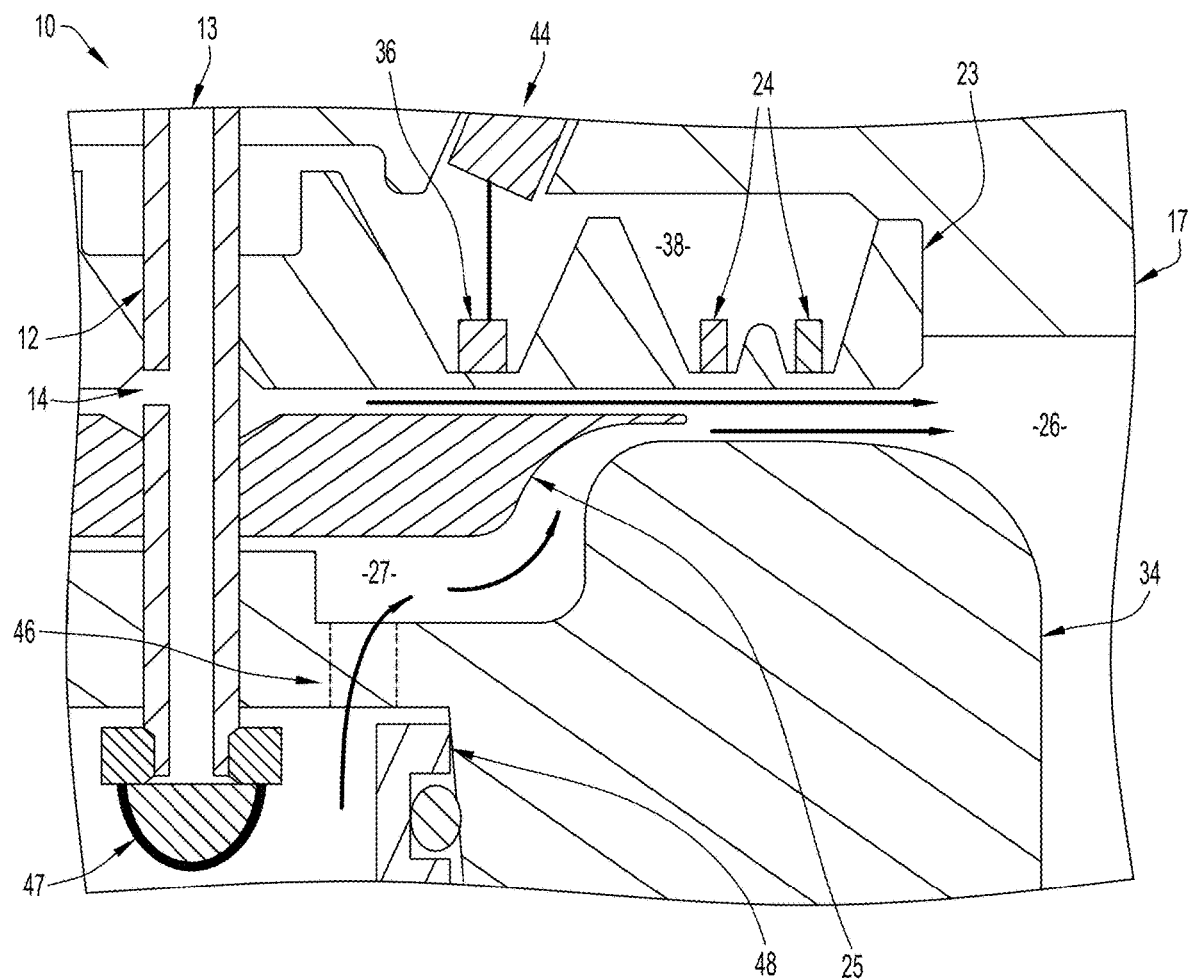
FIG. 5 is an enlarged cross sectional view of a plasma reactor showing gas and liquid flow paths.

The drawing figures do not limit the current invention to the specific embodiments disclosed and described herein.

The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the current invention. The following detailed description is, therefore, not to be taken in a limiting sense. The scope of the current invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

Positional and directional terms, such as "upper", "top", "lower", "bottom", and the like, are used herein to describe various aspects of the current invention as shown in the accompanying figures. While the figures depict the invention in a particular orientation, the invention may be utilized in virtually any orientation. The relationship between the components established by the terms still applies when the invention is utilized in an orientation other than that shown in the figures.

Referring to FIGS. 1-5, a plasma reactor 10, constructed in accordance with at least a first embodiment of the current invention, is shown. The reactor 10 generally receives a gas, a liquid, and electrical stimulus as inputs. The gas may be ionized to form a plasma over the liquid which is in contact with the liquid. The ionized gas interacts with the liquid to create an effluent or product. The plasma reactor 10 broadly comprises a lower housing 18, a housing wall 45, an upper housing 17, at least one dielectric element 23, an upper flow spreader 25, a lower flow spreader 34, first electrode(s) 24, a second electrode which may be the lower flow spreader 34 or another second electrode configuration herein described, and a reaction or effluent chamber 26. The reactor may also include an optional pre-ionization electrode 36. An electric field generator may be attached to the first and second electrodes. In cases where an optional pre-ionization electrode is utilized, an electric field generator may be attached to the pre-ionization electrode. The plasma reactor 10 may also include a plurality of gaskets or seals, such as O-ring seals, that are positioned at the interfaces between various components of the reactor 10.

The housings 17, 18, and 45 generally retain the components of the plasma reactor 10, and its shape may be adapted to the system in which it is implemented. The housings may include additional components that adapt the plasma reactor 10 to the system in which it is implemented. In some embodiments, the housing may have a rounded shape with a plurality of sidewalls. The housings 17, 18, and 45 may also include aligned threaded and non-threaded holes 37 to allow for fasteners to assemble the housings 17 and 45 to the lower housing 18. In addition, the lower housing 18 may include a liquid inlet port 20 and a liquid outlet port 21 which may be connected to the liquid inlet tube 19 and liquid outlet tube 22 respectively. The housings and other components may be constructed from metals, plastics, ceramics, or the like.

The upper housing 17 generally retains the first electrode 24, optional pre-ionization electrode 36, high dielectric element 23, and alignment rod 12. The upper housing 17 may have a box shape with a plurality of sidewalls and an internal cavity 38 bounded by the sidewalls.

The internal cavity 38 may be filled with dielectric materials, ceramics, polymers, gases, or the like to provide electrical isolation and suppress undesirable corona discharge from the first electrode 24 to the upper housing 17 and alignment rod 12. The upper housing lid 17 may also have a second opening roughly centered on the housing to allow for a central alignment rod 12 to which the housing lid 17, dielectric element 23, upper flow spreader 25, and second lower flow spreader 34 may be connected, thereby facilitating good alignment between the various reactor components. The alignment rod 12 may have a gas inlet hole 13 roughly centered in the rod which continues through the rod to the gas inlet port 14 which may allow gas to pass through the port into the gas inlet chamber 15. The alignment rod 12 may be made of electrically conductive material which may allow the use of the alignment rod 12 to electrically contact the lower spreader 34. The lower spreader 34 may be made of conductive material and act as the second electrode or may be made from electrically nonconductive materials which may require an alternate second electrode configuration described herein. The use of the lower spreader 34 as an electrode, or an alternate second electrode configuration may depend on the type of liquid and gas reaction desired or other design considerations.

An optional gas pre-ionization electrode 36 may be included to enable the gas entering the reactor to be ionized prior to entering the reactor chamber 26. This may result in a greater degree of gas ionization. In these cases the upper flow spreader 25 may be made of material such as ceramics or metals that pass the electric field to the area generally under the pre-ionization electrode 36. The pre-ionization electrode 36 may be connected to a second electrical source or use the same source as the first electrode 24. In some cases the first electrode may simply be extended over the upper flow spreader 25 to facilitate this function. This pre-ionization electrode 36 may not be required in all reactors and is optional depending on the reactor requirements.

The first electrode 24 and lower flow spreader 34 or alternate second electrodes may be spaced apart, and the electric field may exist between the two components. Both components 24 and 34 or alternate second electrode may be connected to an external voltage supply which controls the characteristics of the electric field. The voltage supply may provide a plasma generating voltage up to 150 kV of pulsed DC, AC, or other wave form used to create a plasma. In various embodiments, the first electrode 24 and optional pre-ionization electrode 36 may be connected to a variable voltage through the wire 11 and 44 respectively, while the lower flow spreader 34 may be connected as a second electrode or alternate second electrode may be connected to an electrical ground or neutral through the alignment rod.

The first electrode 24 may be annular or ring-shaped, although other shapes are possible, and may be constructed from a metal, such as iron, nickel, gold, copper, alloys thereof, or the like. The first electrode 24 may be located in the internal cavity 38 and may be isolated from the reactor chamber 26 by the dielectric element 23.

The lower flow spreader 34 or alternate second electrode may be generally cylindrically shaped and attached to the alignment rod. In some applications the location of the second electrode may not be critical, and the second electrode may be placed as convenient for the design of the reactor farther away from the first electrode 24. In some embodiments where the liquid may not be electrically conductive, or for other process purposes, the second electrode may be shaped the same as the first electrode 24 and positioned to align with the first electrode within the body of a nonconductive lower spreader 34, as described in more detail below. Given the shapes and orientation of the first electrode 24, pre-ionization electrode 36 and lower flow spreader 34 or alternate second electrode, the electric field generated may be roughly cylindrical in shape and positioned roughly below the respective electrode.

The dielectric element 23 generally provides an insulating gap across which at least a portion of the electric field is established. The dielectric element 23 may be planar and disc-shaped, although other shapes are possible, and may be constructed from insulating dielectric material well known in this field such as ceramics, polymers, or the like. In addition, the first electrode 24 and optional pre-ionization electrode 36 may be plated, deposited, bonded, glued, or otherwise affixed to the upper surface of the dielectric element 23.

The upper flow spreader 25 generally allows the gas to enter the reactor chamber 26 through gas inlet port 13, alignment rod 12, gas inlet port 14, and gas inlet chamber 15 in a roughly radial pattern between the upper flow spreader and the dielectric element 23 and allows liquid to flow roughly evenly in a radial pattern over the lower flow spreader into the reactor chamber 26. The upper flow spreader 25 may have a generally conical shape with a center hole which may allow the upper flow spreader to be mounted on the alignment rod 12.

The lower surface of the upper spreader 25 and upper surface of the lower spreader 36 may create a liquid inlet chamber 27 and may be shaped such that the liquid entering the liquid inlet chamber from the inlet coupler 48 through the water inlet opening 46 exits the inlet chamber 27 radially outward on the surface of the lower spreader 34 into the reactor chamber 26.

At the first upper end of the upper flow spreader 25, the inner surface may be enlarged away from the alignment rod 12 and may create a gas inlet chamber 15. The alignment rod may be hollow to facilitate the passage of gas from the inlet port and may have an opening forming a gas outlet port 14 near the gas inlet chamber 15 which may allow gas to flow through the alignment rod into the gas inlet chamber 15. The lower end of the alignment rod 12 may have the gas blocked with a cap nut 47 or other means such that the gas may not pass through the alignment rod to the inlet coupler 48.

The upper flow spreader 25 may be positioned opposite the dielectric element 23, such that there is a small space between the lower surface of the dielectric element 23 and a top of the upper flow spreader 25. The upper flow spreader 25 may also be positioned concentrically with the first electrodes 24 and optional pre-ionization electrode 36. Gas may flow into gas chamber 15 and may flow radially out to the reactor chamber 26.

The combination of the upper flow spreader 25 and the lower flow spreader may also facilitate the flow of liquid from the liquid inlet chamber 27 to the reactor chamber 26. The inner area of the lower flow spreader 34, in combination with the lower surface of the upper flow spreader 25, may generally establish a radial flow pattern for the liquid before entering the reaction chamber 26. The lower flow spreader 34 may have a generally cylindrical shape with a circumferential sidewall. The upper flow spreader 25 may be positioned within the hollow interior of the housing wall 45, such that the upper flow spreader 25 is concentric with the lower flow spreader 34. There may be a space between the outer surface of the upper flow spreader 25 and the lower flow spreader 34 which forms a liquid passageway. Accordingly, this liquid passageway may allow the liquid to flow from the liquid inlet chamber 27 to the reactor chamber 26. The top edge of the lower flow spreader 34 may be flat, rounded, arcuate, or curved between the inner surface and the outer surface, or tapered from the inner surface to the outer surface.

The bottom edge of the lower flow spreader 34 may be closed except for one or more liquid inlet openings 46 which may facilitate the flow of a liquid from the liquid inlet port 19 through the inlet port 20 and inlet connection tube 48 into the liquid inlet chamber 27. The lower housing 18 may further include one or more liquid inlets 20 and liquid inlet tubes 19 that supply liquid to the reactor 10.

Furthermore, the combination of the dielectric element 23, the upper flow spreader 25, and the lower flow spreader 34 may create a gas flow and a parallel liquid flow where the gas is maintained at slightly greater pressure than the liquid thereby maintaining a gas zone between the high voltage dielectric and the liquid. By maintaining this positive pressure differential, the area of plasma generation may be extended significantly over previous designs.

In some embodiments, the lower flow spreader 34 only may be constructed from electrically conductive materials, such as metals. In such embodiments, the lower flow spreader 34, particularly the upper edge, may form the second electrode. In other embodiments, the lower flow spreader 34 may be constructed from non-conductive materials, such as plastics or ceramics. With these embodiments, the second electrode may be formed either by the alignment rod 12, the cap nut 47, or a second annular electrode made of electrically conductive material located at the top of the lower spreader generally below the first electrode or electrically isolated by a second electrode dielectric from the liquid. In cases where the liquid is conductive to AC waveforms, the location of the second electrode may be remote and even outside the reactor 10 using such things as a conductive liquid outlet or inlet tube 19 and 22 connected to ground or neutral.

The reactor chamber 26 generally provides a setting for the gas to be ionized while in the general area under the dielectric element 23 and first electrode 24 and to react with the liquid. The reactor chamber 26 may include an outer surface and an inner surface. The outer surface may be bounded by the lower surface of the dielectric element 25, the lower surface of the upper housing 17, the inner surface of the housing wall 45, and the upper surface of the lower housing 18. The inner surface may be bounded by the outer edge of the upper flow spreader, the outer edge of the lower flow spreader 34, and the outer surface of the inlet coupler 48.

The plasma reactor 10 may operate as follows: the liquid inlet tube 19 may be coupled to an external pressurized liquid source which may be pressurized between 2 and 300 pounds per square inch gauge (psig). The gas inlet 13 in the alignment rod 12 may be coupled to an external pressurized gas source, the gas may be supplied at a positive pressure relative to the liquid source pressure, and the gas flow rate into the gas inlet 13 may be somewhat controlled.

The gas may flow from the gas inlet 13 into the alignment rod 12 and through the alignment rod 12 through the gas inlet port 14 into the gas inlet chamber 15. From here the gas may flow from the gas inlet chamber 15 between the upper flow spreader 25 and the high voltage dielectric element 23 radially outward into the reaction chamber 26, thereby creating a gas layer.

As the gas passes through the electric field, a plasma may be created which ionizes the gas and converts it into a stream of plasma with roughly laminar flow with the liquid. The characteristics of the electric field may be controlled by the external voltage supply which may provide a plasma generation voltage of up to 150 kV AC, pulsed DC, or other electrical plasma generating sources familiar to those in the industry. The strength of the electric field is generally the greatest at the shortest distance between the first electrode 24 and the surface, slightly below the surface of the liquid, or the second electrode 29, which may be generally below the first electrode 24.

The liquid may flow from the liquid inlet tube 19 through inlet 20 and inlet coupler 48 through the liquid inlet openings 46 in the lower spreader into the liquid inlet chamber 27. Given the curvature of the bottom of the flange 39 and the curvature of the top edge of the lower flow spreader 34, the liquid may exit the liquid inlet flow chamber 27 and flow radially outward in the channel formed by the upper flow spreader 25 and the lower flow spreader 34 into the reactor chamber 26. The liquid may then flow through the electric field with the gas as a stream with roughly laminar flow. The gas may flow on top of the liquid stream through the electric field forming a plasma. As the liquid and the plasma flow through the electric field, some of the ions created in the plasma and some other non-ionized gas may react or otherwise enter the liquid to create a stream of effluent. The effluent flows outward from the center of the reactor 10 and is collected toward the bottom of the reactor chamber 26. The effluent may exit the plasma reactor 10 through the liquid outlet port 21 located at the bottom of the reactor chamber 26 and into the liquid outlet tube 22.

Figure 6:
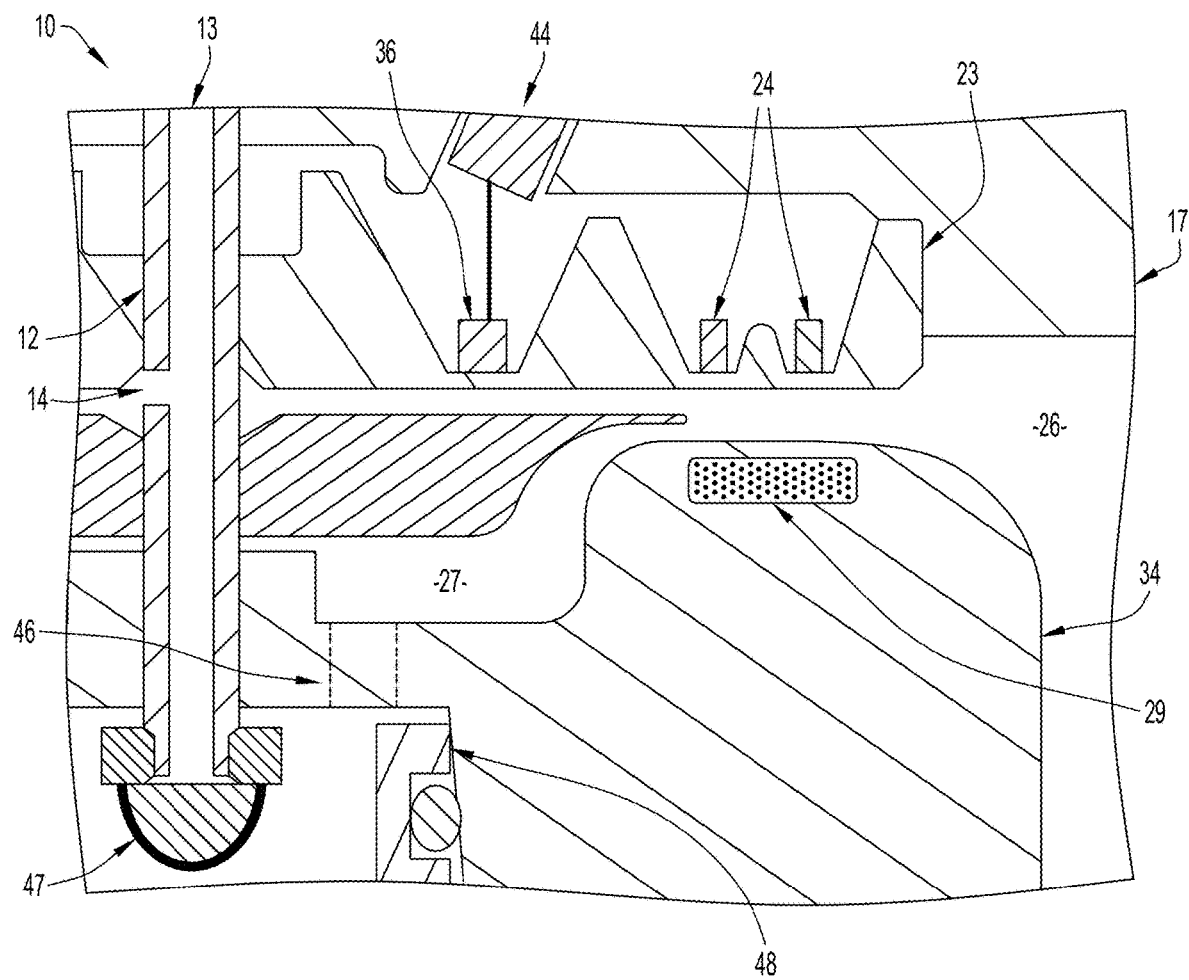
FIG. 6 is the enlarged cross sectional view of a plasma reactor of FIG. 5 showing the second embodiment of the plasma reactor showing a dielectrically isolated second electrode.

Referring to FIG. 6, a second embodiment of the reactor utilizes a dielectrically isolated second electrode 29. In some applications which may include oxygen and ultra-high purity water, it may be desirable to avoid any liquid contact with metallic elements or elements that are conducting electricity. Other applications where this is desirable may include applications where the liquid is not able to be connected to an electrical potential. There are other applications that may benefit from a dielectric isolation not listed here. In these applications the second electrode may be dielectrically isolated from the liquid by using a second electrode 29. This electrode may be placed in the lower flow spreader 34 and covered with a material such as ceramic, polymer, or other materials known by those familiar with the art to isolate the alternate electrode 29 from the liquid stream. In these cases the electrical field will be shared by the dielectric element 23, the gas flow below the dielectric element, the liquid above the lower flow spreader 34, and the material used to isolate the alternate second electrode 29.

Figure 7:
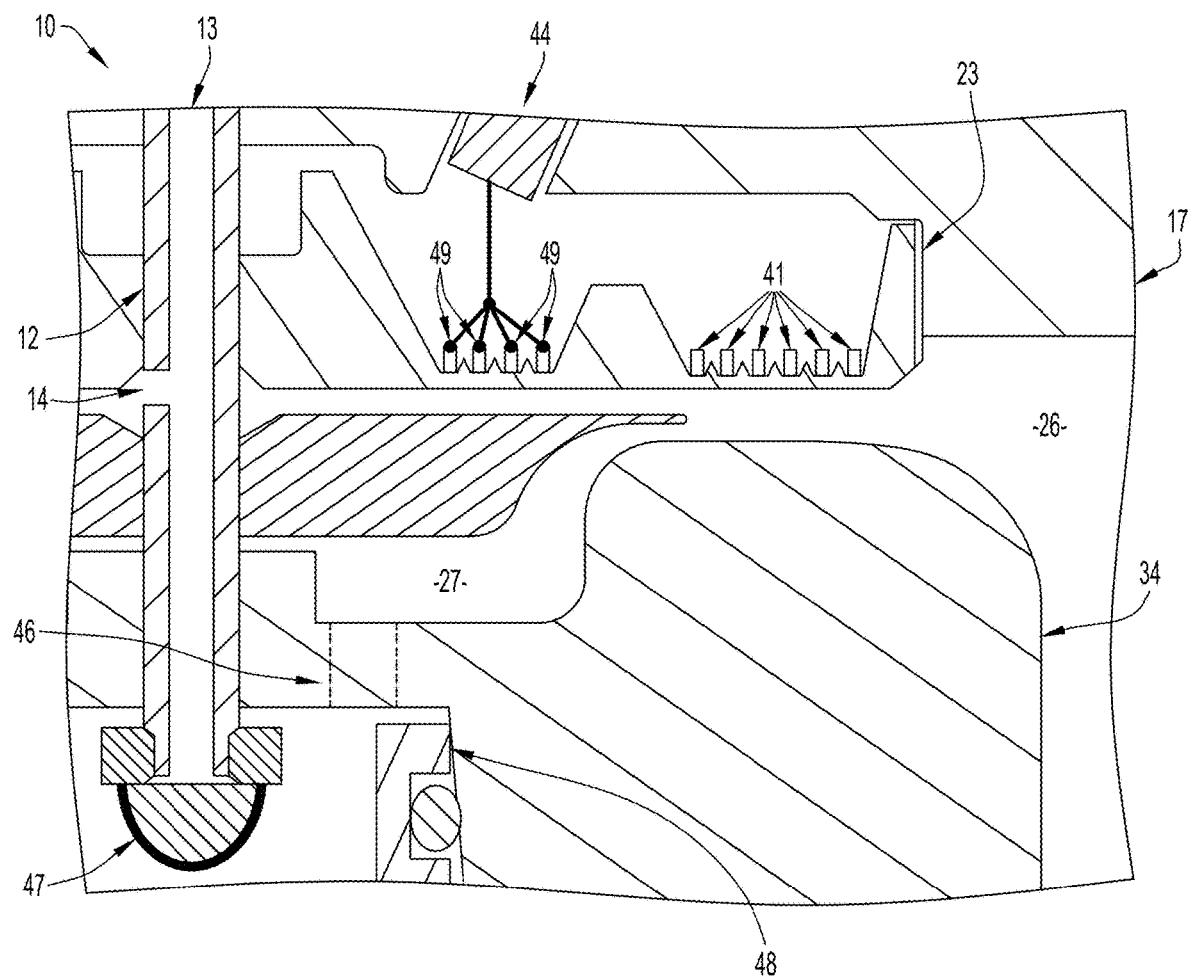
FIG. 7 is the enlarged cross sectional view of a plasma reactor of FIG. 5 showing a reactor with multiple electrodes on the pre-ionizer and first electrode.

Referring to FIG. 7, a third embodiment of this reactor may split the first electrode into several alternate first electrodes 41. These alternate first electrodes 41 may be annular or other shapes, may be located in the internal cavity 38, and may be isolated from the reactor chamber 26 by the dielectric element 23. In addition, this type of electrode may be used for alternate optional pre-ionization electrodes 49. By using multiple electrodes, the electrical characteristic of a reactor of a given size may be altered thereby enabling a greater plasma area without a corresponding increase in electrode capacitance and simplifying the design of the electrical source to drive the electric field required to generate a plasma. One or more first electrodes may be used in a given reactor. One or more optional pre-ionization electrodes may be used in a reactor. The use of a type of one or more first electrodes in a given reactor may depend on the reactor size, type of reaction desired, and/or other considerations. The use of an optional pre-ionization electrode and the configuration of said optional pre-ionization electrodes also may depend on the type of reaction and other design considerations. The use of various configurations of first electrodes and configurations of optional pre-ionization electrodes are interchangeable.

The present invention includes plasma reactor systems having a housing with an internal reaction chamber; at least one electric field generator configured for generating one or more electric fields between electrodes, with at least a portion of an electric field within the reaction chamber; a dielectric element; a gas source; a liquid source; a gas inlet path to the reaction chamber; and a liquid inlet path to the reaction chamber, where the stream of gas and stream of liquid within the reaction chamber are configured to flow adjacent one another and to pass through the electric field to produce an effluent. It is understood that systems embodying the present invention may further include any one, all, or any combination of additional features described herein. Such optional features include, but are not limited to, a pre-ionization electrode for pre-ionizing a gas prior to entry into the reaction chamber, multiple electrodes in series, flow spreaders, an alignment rod, and an effluent outlet path, as described above. Creating a plasma area in a gas adjacent to a liquid accommodates a number of novel uses.

In an embodiment of the present invention, an exemplary use of a plasma reactor for creating a plasma area in a gas adjacent to a liquid includes using oxygen as a feed gas and water as a feed liquid. The oxygen can be pre-ionized prior to entering a reaction chamber 26 via a pre-ionization electric field created by an electric field generator between a pre-ionization electrode 36 and a second electrode 29. Within the reaction chamber 26, ionized oxygen particles are driven into the water via a primary electric field between a first electrode 24 and a second electrode 29 to either disinfect or oxidize undesirable particles in the water, oxygenate the water, or leave a residual level of hydroxyls, ozone, hydrogen peroxide, or other particles in the water.

Figure 8:
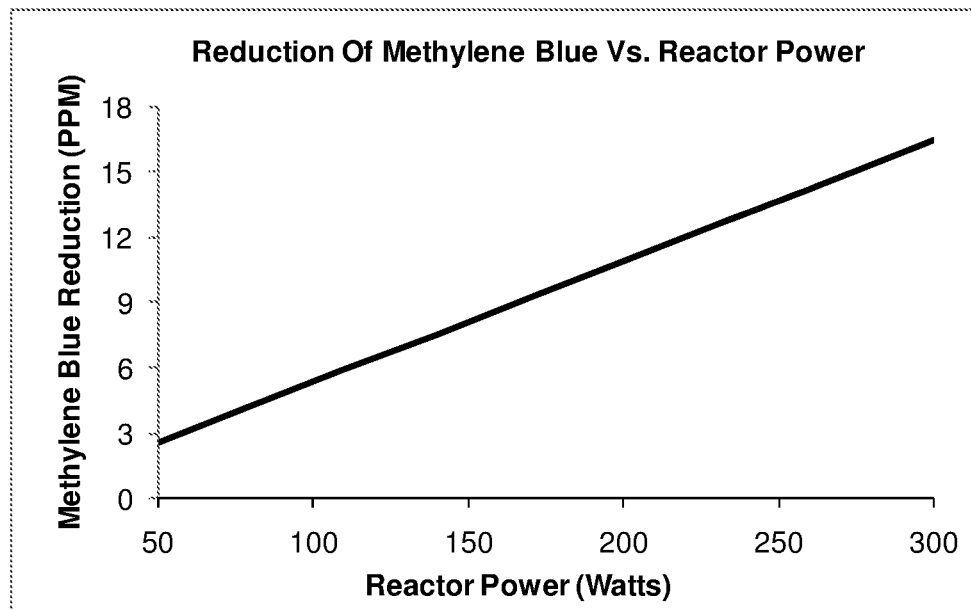
FIG. 8 is a graph of methylene blue reduction in reactor effluent water vs. reactor power using oxygen as a feed gas.

FIG. 8 shows the effect of treatment of water doped with Methylene Blue with a plasma reactor of the present invention, using oxygen as a feed gas. Methylene Blue, also known as methylthioninium chloride, is a medication and dye used in the industry as a surrogate for contamination in water. Levels of Methylene Blue can be measured using ultraviolet-visible spectroscopy (UV/VIS) or other equipment. FIG. 8 shows the capability of a plasma reaction of the present invention to reduce or eliminate contaminates in the effluent liquid. Additionally, it demonstrates that the level of disinfection may be altered or controlled by the power supplied to the reactor via the plasma voltage generator.

Figure 9:
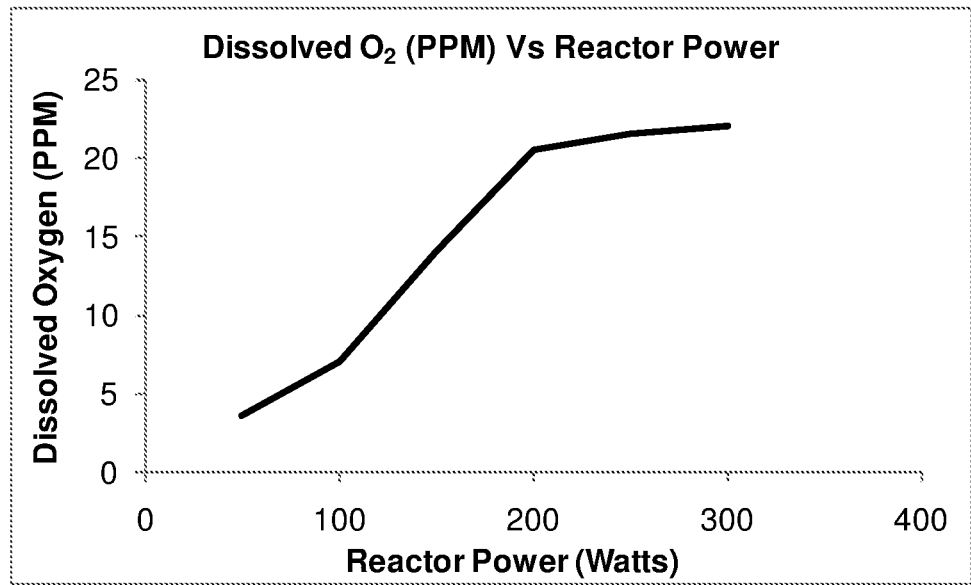
FIG. 9 is a chart of residual dissolved oxygen in effluent water after treatment with an oxygen feed gas.
Figure 10:
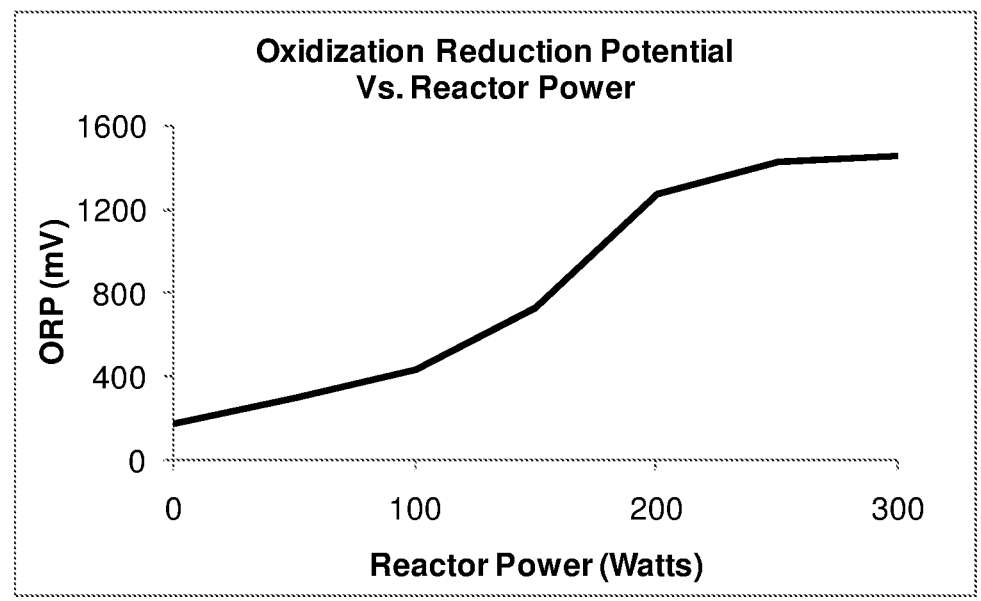
FIG. 10 is a chart of oxidization reduction potential of an effluent gas after treatment with an oxygen feed gas.

Another exemplary use of a plasma reactor for creating a plasma area in a gas adjacent to a liquid includes the use of oxygen and water to oxygenate water and/or to create a residual disinfecting effect in the water. FIG. 9 shows an example of the residual dissolved oxygen in effluent water after treatment with oxygen as a feed gas to the plasma reactor. FIG. 10 shows an example of the residual Oxygen Reduction Potential (ORP) of effluent water using oxygen as a feed gas.

A further embodiment of creating a plasma area in a gas adjacent to a liquid includes using nitrogen as a feed gas and water as a feed liquid in order to drive monatomic and non-monatomic nitrogen from the gas into the water. This process creates a nitrogen-containing effluent water.

Figure 11:
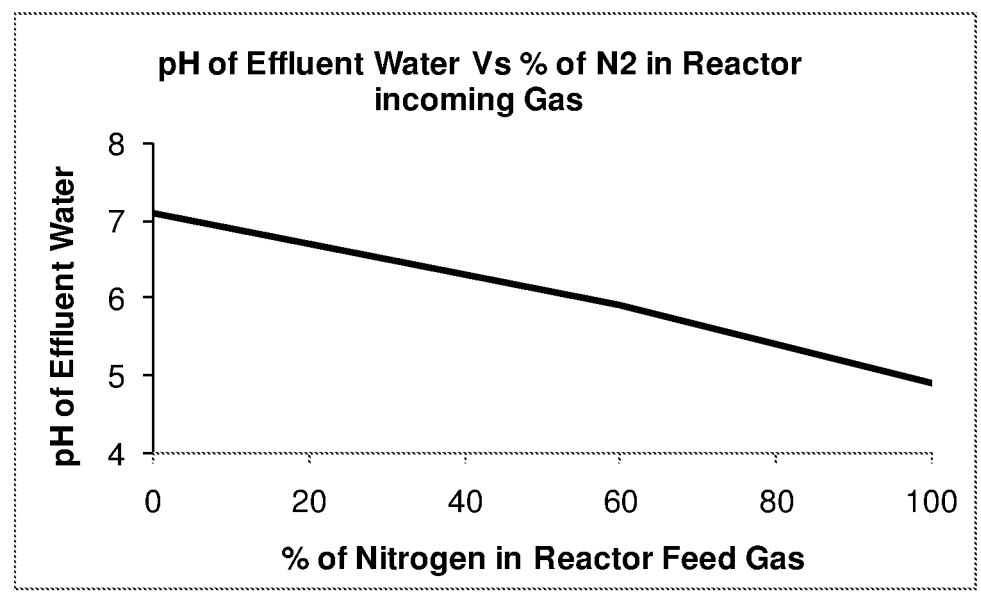
FIG. 11 is a graph using pH to monitor the reactor effluent water vs. nitrogen in the gas (feed gas) fed into the plasma reactor.
Figure 12:
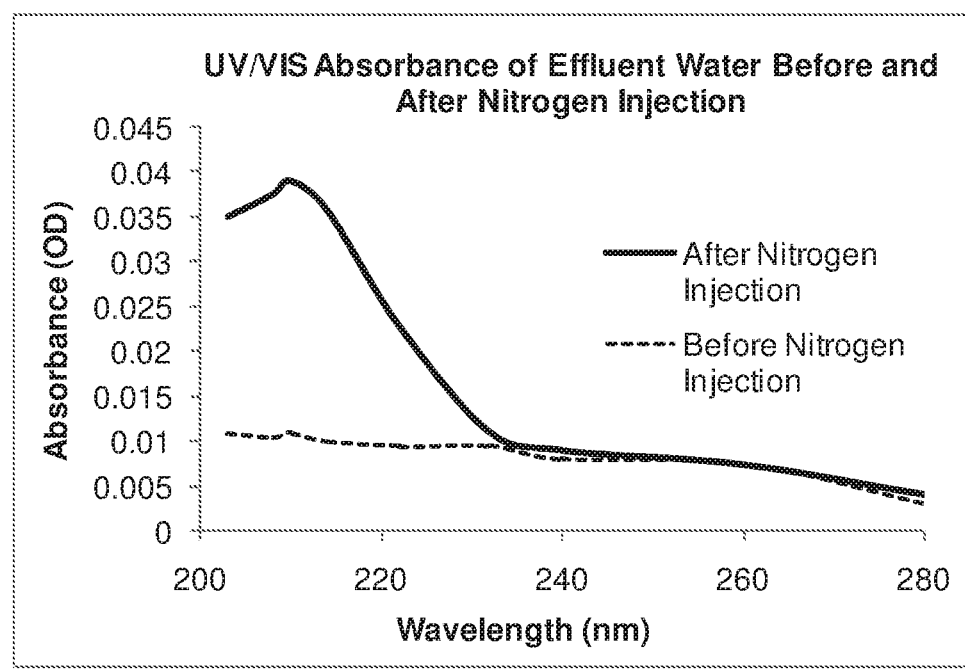
FIG. 12 is a confirmation by ultraviolet-visible spectroscopy (UV/VIS) that levels of nitrogen in the effluent water are increased in the effluent water.

FIG. 11 and FIG. 12 show the effect of water treated with a plasma reactor system of the present invention, using nitrogen as a feed gas. In FIG. 11, the pH of the effluent water is measured for various mixtures of nitrogen and oxygen. This shows that as the percentage of nitrogen in the reactor feed gas is increased, the pH of the effluent water is decreased. FIG. 12 shows the UV/VIS absorbance spectrum of the effluent water after treatment with nitrogen, showing an increased level of nitrogen in the effluent water.

Alternatively, various combinations of nitrogen and oxygen can be used as a feed gas to create a combination of the effects described in the above embodiments. In addition, these methods may allow for positive control of pH in the effluent water.

Figure 13:
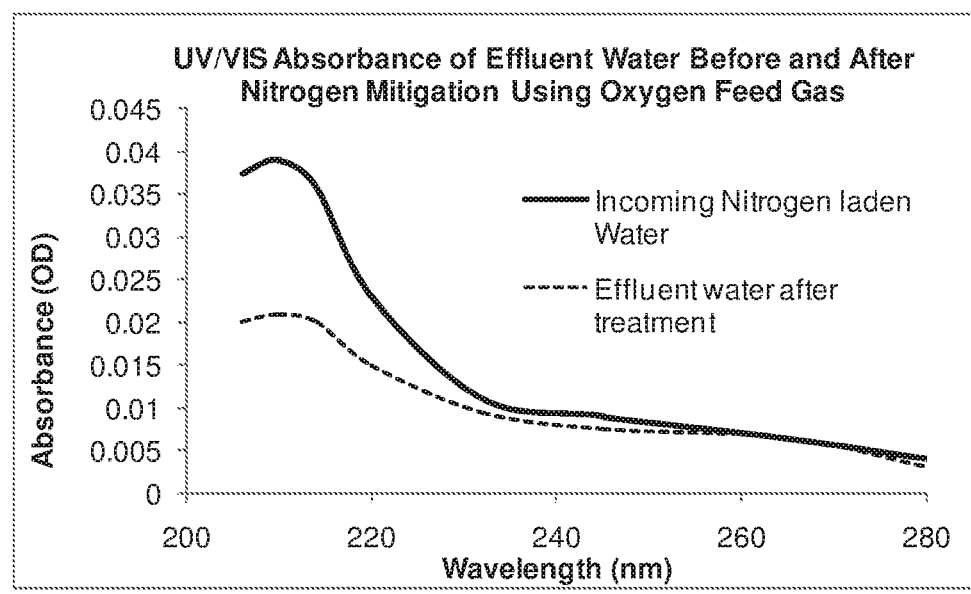
FIG. 13 is a confirmation by graph of ultraviolet-visible spectroscopy (UV/VIS) that levels of nitrogen in the effluent water are decreased after nitrogen-laden water is treated with oxygen as a feed gas.

Another use of a plasma reactor which creates a plasma area in a gas adjacent to a liquid includes using oxygen as the feed gas with water containing nitrogen as the feed liquid. FIG. 13 shows the UV/VIS absorbance spectrum of water containing nitrogen before and after treatment with an oxygen feed gas. FIG. 13 illustrates the capability of using the present invention to control nitrogen levels in effluent liquid to desirable levels for various uses.

An additional exemplary use of a system for creating a plasma area in a gas adjacent to a liquid includes the dissociation of particular components within a gas. For instance, natural gas, methane, and associated fuel gases contain carbon and other unwanted elements and compounds. Such gases can be used as a feed gas in a plasma reactor of the present invention with water or other liquids as a feed liquid to dissociate part or all of the carbon from the feed gas. The plasma reaction within the reaction chamber can further result in the dissociated carbon becoming associated with the water or other liquid allowing for removal from the reactor. Using this technique results in lower levels of carbon dioxide ($CO_2$) emissions when the fuel is subsequently used.

Figures 14, 15:
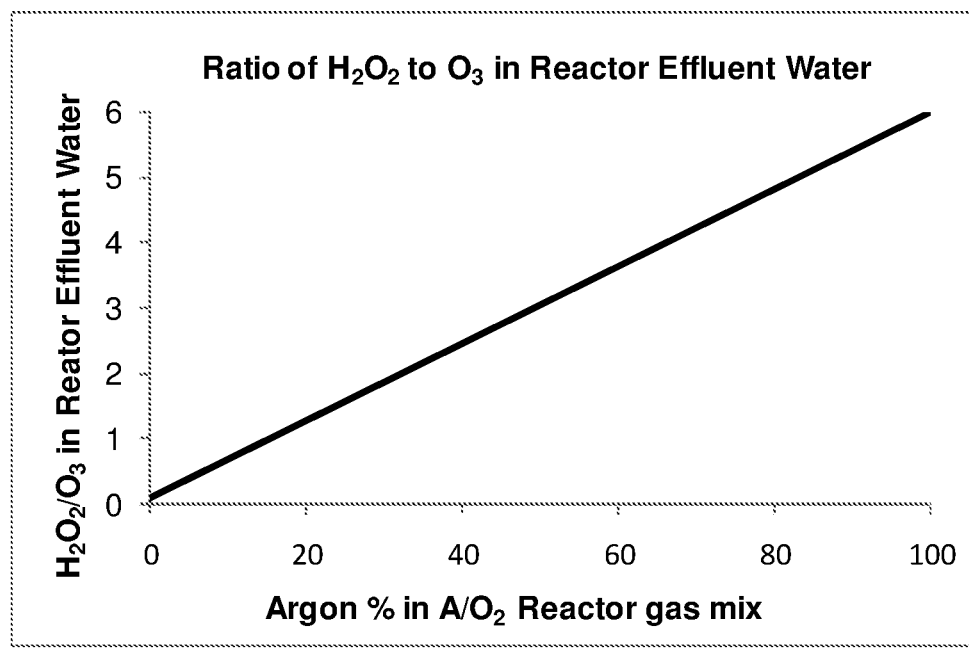
FIG. 14 is a graph of the ratio of hydrogen peroxide ($H_2O_2$) to dissolved ozone (O3) in the reactor effluent water vs. the ratio of argon to oxygen in the reactor gas mixture.
FIG. 15 is a chart of production rates of hydrogen peroxide and hydrogen as a gas or as dissolved hydrogen in the water using argon and argon/hydrogen mixtures as feed gases vs. reactor power.

A further embodiment of a use of a plasma reactor system for creating a plasma area in a gas adjacent to a liquid includes use of a gas which may be ionized, causing the liquid to be modified or re-form desirable molecular structures. FIG. 14 shows the use of argon and argon and oxygen mixtures as feed gases and the resulting hydrogen peroxide ($H_2O_2$) to ozone ($O_3$) ratio in the effluent water. In this manner, the latent disinfection capabilities of the effluent water may be modified.

Another exemplary use of a system for creating a plasma area in a gas adjacent to a liquid includes the use of a gas or a mixture of gases as a feed gas to modify water to create hydrogen peroxide and hydrogen. One example of such a use includes, but is not limited to, use of argon or a mixture of argon and hydrogen as a feed gas. FIG. 15 shows the results of the rate of production of hydrogen peroxide and hydrogen using a plasma reaction of the present invention using argon and argon and hydrogen mixtures as feed gases vs. reactor power. The hydrogen produced may be dissolved hydrogen in the water, hydrogen gas, or a combination of both.

In an embodiment of the present invention, a gaseous particle injection system and method is configured for injecting or infusing gaseous particles into a liquid. In this embodiment, the reactor includes a reaction chamber for holding a liquid and a gas adjacent to the liquid. The reactor further includes first and second electrodes configured for forming an electric field between them, at least a portion of the electric field being positioned within the reaction chamber. A desired feed liquid is inserted into the reaction chamber through an inlet path, and a desired feed gas is inserted into the reaction chamber adjacent to the liquid through an inlet path. The feed liquid(s) and feed gas(es) may be flowing or non-flowing during a reaction in a reactor embodying the present invention. The reactor is connected to a power source, and a voltage is applied between the first and second electrodes, forming an electric field at least partially positioned within the reaction chamber. In a preferred embodiment, the connected power source is configured for producing an alternating current (AC), however, alternatively, pulse direct current (DC) or another wave form can be used.

The electric field makes contact with the gas and liquid within the reaction chamber, injecting or infusing particles from the feed gas into the liquid, forming a desired effluent with injected or infused gaseous particles. The power of the electric field can be adjusted to optimize production of the desired effluent. For instance, utilizing voltages below the ionization energy or minimum power required to ionize the feed gas may result in increased ratios of molecular gas being injected or infused into the liquid. Utilizing higher voltages may result in higher levels of ionic gas injection. By varying electrical field strength of these systems, the ratio of molecular injection or infusion to ionic injection into the feed liquid can be controlled.

In an exemplary embodiment, water is the feed liquid and molecular oxygen is the feed gas to a reactor of the present invention. By reducing or modulating the power of the reaction, levels of Oxidation Reduction Potential (ORP) and dissolved oxygen in the effluent can be independently controlled to some extent, as desired for the particular intended use of the effluent. Alternatively, other feed gases and feed liquids may be used in reactors and reactions embodying the present invention. For instance, nitrogen or argon may be used as a feed gas for reactions of the present invention. Furthermore, combinations of multiple gases and/or combinations of multiple liquids could be used as feed gases and/or feed liquids, respectively.

Figure 16:
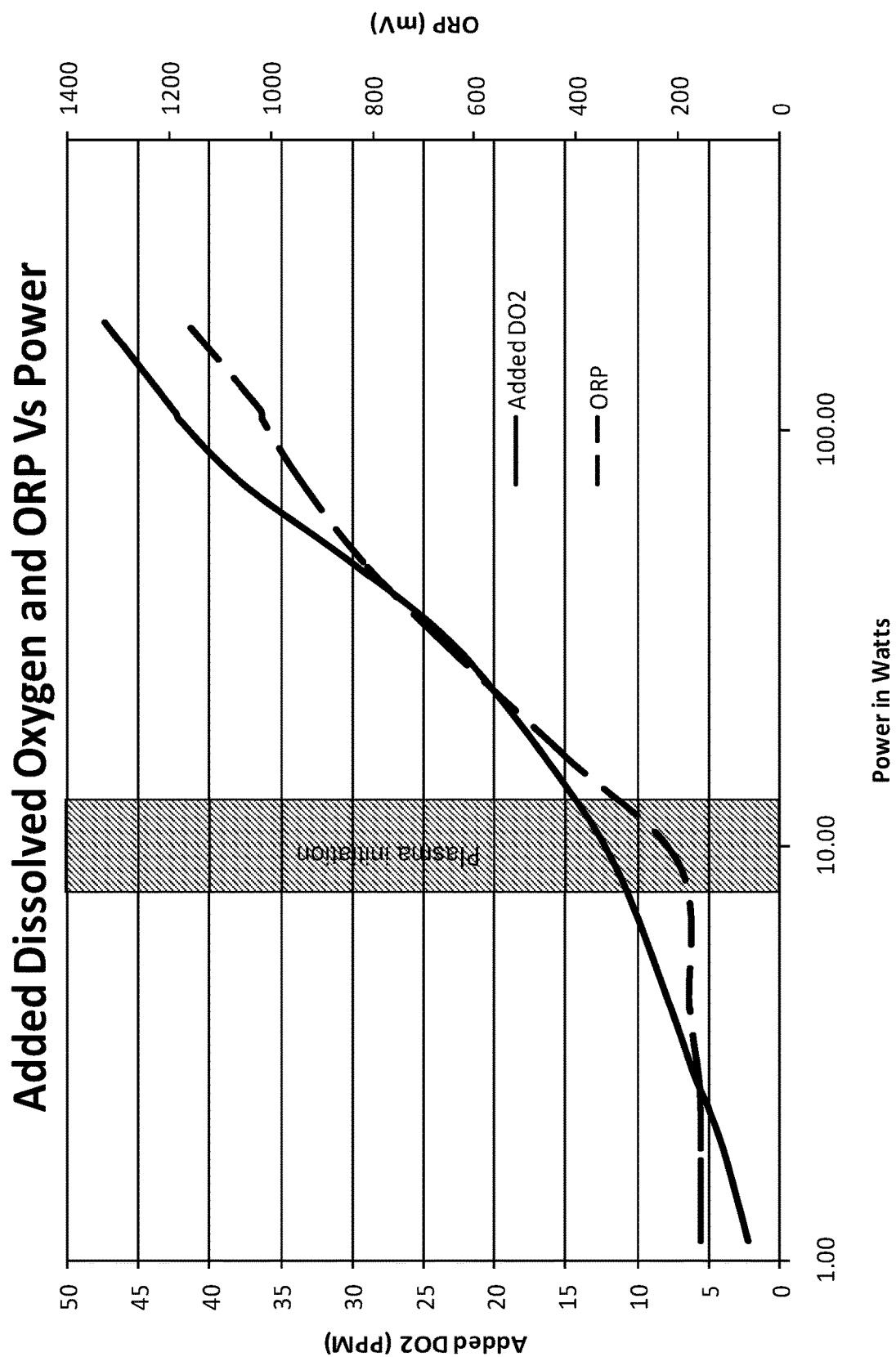
FIG. 16 is a graph showing dissolved oxygen ($DO_2$) and oxidation reduction potential (ORP) in effluent water vs. power using a reactor of the present invention. $DO_2$ is monitored using a dissolved oxygen meter, and ORP is used to monitor oxidization radicals such as dissolved ozone formation after initiation of plasma in the reactor. This embodiment of the reactor is using water as a liquid and oxygen as a feed gas.
Figure 17:
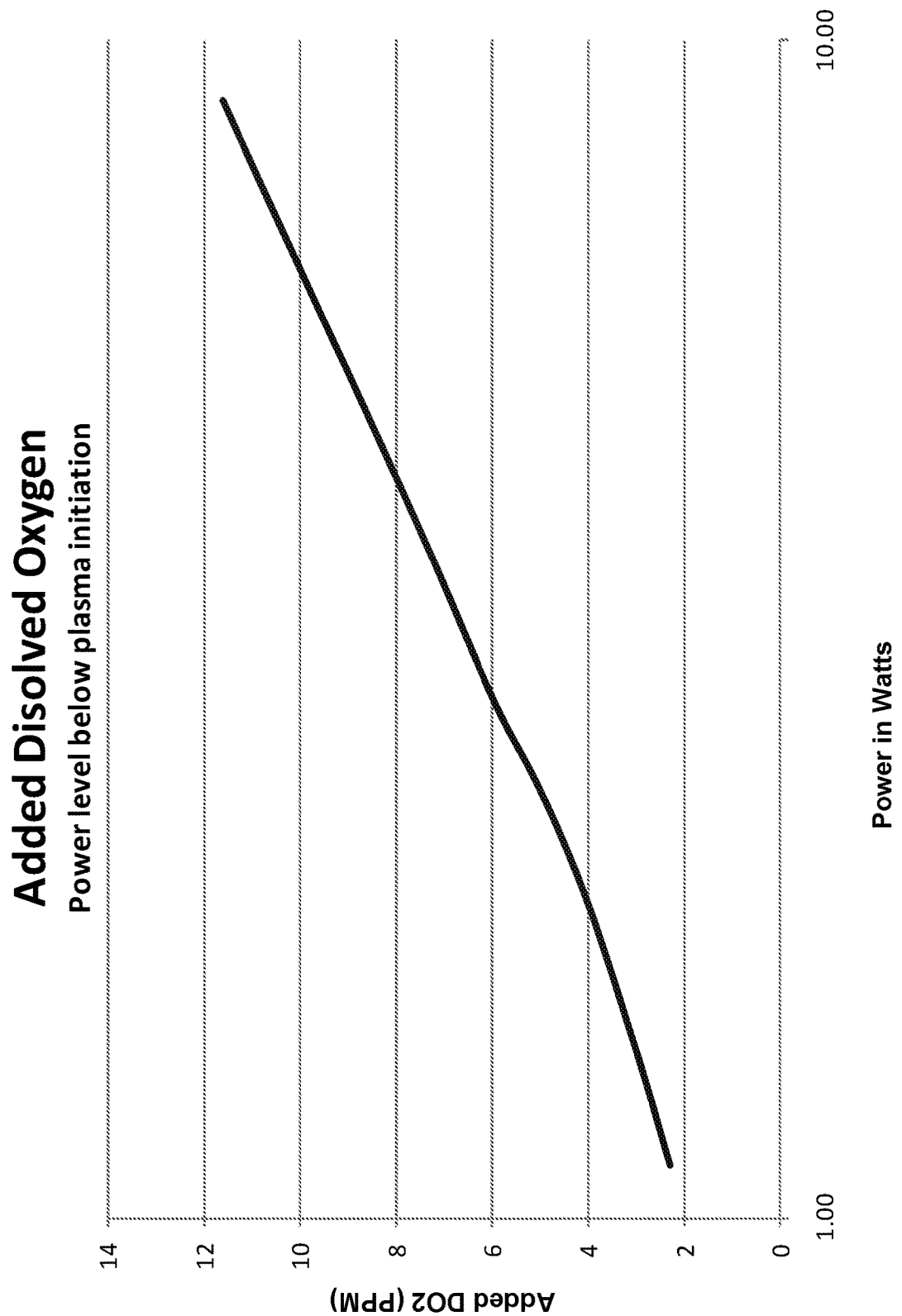
FIG. 17 shows the infusion of oxygen into the liquid at voltage generator power levels below the power required to ionize the gas and inject oxygen radicals into the liquid.

An embodiment of use of a reactor of the present invention with a gas adjacent to a liquid and an electrical field is demonstrated by FIGS. 16 and 17, with water being the feed liquid and oxygen being the feed gas. In a reaction embodying the present invention, dissolved oxygen ($DO_2$) was monitored using a dissolved oxygen meter and ORP was used to monitor oxidation of radicals, such as dissolved ozone formation, at power levels higher than voltage to initiate plasma in the reactor. FIG. 16 shows that dissolved oxygen is infused into the liquid at power levels both below and above the power levels required for initiation of plasma. However, both molecular oxygen ($O_2$) and oxygen radicals, which increase the ORP, are infused at power levels above the power levels required for initiation of plasma.

FIG. 17 shows a graph displaying oxygen infusion at power levels below the electrical field intensity required for initiation of a plasma. The embodiment of the present invention shown in FIGS. 16 and 17 accommodates a method of infusing oxygen into a liquid without ionizing the gas such that oxygen radicals are not injected into the liquid.

By running the reactor at a power level less than or close to the level of power required to fully ionize the gas, as shown in FIG. 17, molecules of the gas can be infused into the liquid, resulting in a modified effluent liquid. To demonstrate this embodiment, oxygen was infused at low power levels to increase the dissolved oxygen content in a stream of water. This allows dissolved oxygen levels to be increased in the water independently of increases in ionic injection.

The aforementioned use examples are for illustrative purposes only to demonstrate the capability of systems which create a flow of liquid adjacent to a gas with the capability of creating a plasma in the gas. These examples may be generally referred to for clarity, but not limited to, the following categories of reactions: ionic injection, gas dissociation, liquid re-formation, and liquid dissociation.

Those skilled in the art shall understand that various combinations of feed gas and liquids may result in many desirable gas and liquid effluent products from this type of plasma reactor system. The capability to control effluents has been shown above based on a combination of the feed gas mixture used, the liquid used, and the reactor conditions, such as power, voltage, pressure, flow rates, and other reactor parameters.

The reactor system and method of the present invention can be used for a variety of medical applications. Without limitation, medical applications include:

1) Immunization (Immuno) Therapy. Such therapies can be administered or enhanced with the present invention for controlling infectious and contagious diseases, including coronavirus (Covid 19), influenza, etc.
2) Wound Treatment. Wound healing generally can be facilitated using ionized solutions with nano-particles produced by the present invention. For example, wound closure, reepithelialization and tissue regeneration are enabled and enhanced.
3) Cancer Treatment. The present invention maintains higher oxygen levels cells to retard reproduction of cancer cells. The ionized solution nano-particles are small enough that they avoid detection by the cancer cells when injected into patients' blood streams and thereby block or inhibit further cancer cell reproduction at tumor sites.
4) Disinfectant. Ionized solutions produced according to the present invention has effective disinfectant properties.

Although the invention has been described with reference to the embodiments illustrated in the attached drawing figures, it is noted that equivalents may be employed and substitutions made herein without departing from the scope of the invention as recited in the claims.

Having thus described the invention, what is claimed as new and desired to be secured by Letters Patent is:

1. A method of injecting ionic particles from a gas into a liquid with a reactor including first and second electrodes connected to a power source and configured for forming an electric field therebetween, the method comprising:

inserting said liquid into a reaction chamber of the reactor;

inserting a high-pressure flow of said gas into said reaction chamber at a positive pressure relative to a pressure of said liquid in said reaction chamber, wherein the positive pressure enables the high-pressure flow of said gas to enter adjacent to said liquid;

applying a series of voltage pulses between said first and second electrodes and thereby producing said electric field, wherein at least a portion of said electric field is positioned within said reaction chamber; and adjusting a magnitude of said voltage pulses and thereby controlling a ratio of man-atomic ions to molecular ions, said electric field contacting said gas and said liquid within said reaction chamber; and said ionic particles from said gas being transferred into said liquid to form a medical treatment effluent comprising said liquid infused with dissolved gas.

2. The method of claim 1, wherein said medical treatment effluent is usable for vaccinating patients.

3. The method of claim 1, wherein said medical treatment effluent is configured for wound treatment consisting of one or more of: tissue closure; reepithelialization; and skin grafting.

4. The method of claim 1, wherein said medical treatment effluent is configured for cancer treatment by injecting into patients' blood streams for blocking cancer cell growth at tumor sites.

5. The method of claim 1, wherein said medical treatment effluent is usable for disinfecting applications.

6. The method of claim 1 wherein:
said gas comprises oxygen; and
said liquid comprises water.

7. The method of claim 6, wherein:
said ionic particles from said gas being transferred into said liquid comprise ions from said oxygen being transferred into said water.

8. The method according to claim 1, wherein the reactor further includes a pre-ionization electrode connected to said power source while dielectrically isolated from said first electrode and positioned outside the reaction chamber, the method further comprising:
applying a voltage between said pre-ionization electrode and said second electrode producing a pre-ionization electric field within said reactor and outside said reaction chamber; and
flowing said high-pressure flow of said gas through said pre-ionization electric field prior to entry into said reaction chamber, partially ionizing said gas prior to said entry into said reaction chamber.

* * * * *